United States Patent [19]

Watanabe et al.

[11] 4,321,161
[45] Mar. 23, 1982

[54] LIQUID-ABSORBING SHAPED BODY

[75] Inventors: Yoshiaki Watanabe, Hikari; Genji Taga, Shinnanyo; Takanori Teshima, Tokuyama, all of Japan

[73] Assignee: Tokuyama Soda Kabushiki Kaisha, Yamaguchi, Japan

[21] Appl. No.: 178,295

[22] Filed: Aug. 15, 1980

[30] Foreign Application Priority Data

Aug. 18, 1979 [JP] Japan .............................. 54-104528

[51] Int. Cl.$^3$ ....................... B01J 27/02; B01J 37/00; B01J 31/02; B01J 29/00
[52] U.S. Cl. .................................... 252/440; 252/425; 252/427; 252/454; 106/109
[58] Field of Search ................ 252/425, 427, 440, 454

[56] References Cited

U.S. PATENT DOCUMENTS 1,851,204  3/1932  Moreton ............................. 252/440
4,282,115  8/1981  Atsukawa et al. .................. 252/440

Primary Examiner—Delbert E. Gantz
Assistant Examiner—William G. Wright
Attorney, Agent, or Firm—Sherman & Shalloway

[57] ABSTRACT

Disclosed is a liquid-absorbing shaped body comprising a fibrous material and an inorganic powder in which the volume of fine pores having a pore radius less than $0.5\mu$ is at least 2.5 cc/g. This shaped body is excellent in the liquid-absorbing capacity and liquid-retaining property to various kinds of liquids.

13 Claims, No Drawings

LIQUID-ABSORBING SHAPED BODY

BACKGROUND OF THE INVENTION (1) Field of the Invention

The present invention relates to a novel liquid-absorbing shaped body. More particularly, the present invention provides a liquid-absorbing shaped body excellent in both the liquid-absorbing capacity and the liquid-retaining property.

(2) Description of the Prior Art

As the liquid-absorbing material, there have been used shaped fibrous bodies obtained by wet-forming fibers such as pulp fibers and rayon fibers under a low pressure, such as absorbent papers.

However, although these fibrous shaped bodies are excellent in the liquid-absorbing capacity, that is, the amount of the absorbed liquid (liquid absorbability) and the liquid-absorbing rate, they are very poor in the liquid-retaining property. Accordingly, when a conventional absorbent paper such as mentioned above is used as blotting paper, there is observed a disadvantage that if ink on paper is absorbed by the absorbent paper and it is intended to absorb ink again with the same portion of the absorbent paper, the previously absorbed ink is caused to ooze out by the pressure for applying the absorbent paper to the paper surface.

Various starch-modified polymers such as starch-acrylic acid ester copolymers have recently been proposed as liquid-absorbing materials. These startch-modified polymers are especially excellent in the liquid absorbability to water and have a relatively good liquid-retaining property.

However, these starch-modified polymers are defective in that since the starch-modified polymers extremely swell on absorption of liquids, liquid passages are closed especially when particles of the starch-modified polymers are present in the state where they are brought in close proximity to one another, resulting in reduction of the liquid-absorbing speed. Moreover, it is very difficult to shape these starch-modified polymers into certain forms. Accordingly, such polymer is inevitably used in the powdery form, and hence, the application fields and methods are limited. Although the liquid absorbability of such starch-modified polymer to water is excellent, the liquid absorbability to an inorganic salt aqueous solution or organic solution is ordinarily very poor.

BRIEF SUMMARY OF THE INVENTION

As the result of our researches made with a view to overcoming the defects of the above-mentioned absorbing materials, we found that a shaped body comprising an inorganic powder containing a specific amount of specific fine pores and a fibrous material has an excellent liquid-retaining property that cannot be expected from the poor liquid-retaining property of the above-mentioned conventional fibrous shaped bodies and this shaped body also has an excellent liquid-absorbing capacity. Based on these findings, we have now completed the present invention.

In accordance with the present invention, there is provided a liquid-absorbing shaped body comprising a fibrous material and an inorganic powder composed of aggregated slices in which the volume of fine pores having a pore radius less than $0.5\mu$ is at least 2.5 cc/g.

In the instant specification and appended claims, the values of the pore radius and pore volume are those determined by using a mercury porosimeter.

Shaped bodies for use in absorbing liquids, which comprise a fibrous material and an inorganic powder, have hardly been proposed. The reason is as follows.

In fibrous shaped bodies such as mentioned above, efforts for increasing voids among fibers have been made so as to increase the liquid absorbability. Accordingly, it is considered that incorporation of an inorganic powder into such fibrous shaped body to be used for absorbing liquids, for example, absorbent paper, will result in reduction of the liquid absorbability of the fibrous shaped body because the above-mentioned voids among fibers are filled with the inorganic powder. Therefore, ordinarily, an inorganic powder has not been incorporated into fibrous materials to be used for absorbing liquids.

From such technical background of fibrous shaped articles for absorbing liquids, it will readily be understood that the liquid-absorbing shaped body of the present invention comprising a fibrous material and a specific inorganic powder is a novel liquid-absorbing material.

The liquid-absorbing shaped body of the present invention comprises a fibrous material and an inorganic powder. In the shaped body of the present invention, the fibrous material mainly forms liquid passages for promptly absorbing liquids, and the inorganic powder mainly exerts a function of retaining liquids introduced into the shaped body in fine pores thereof. The mechanism of retention of a liquid in fine pores of the inorganic powder is quite different from the mechanism of retaining a liquid in voids among fibers in the conventional fibrous shaped body, and this difference of the liquid-retaining mechanism is manifested as an obvious difference of the liquid-retaining capacity between the shaped body of the present invention and the conventional fibrous shaped body. More specifically, the liquid retained in the voids among fibers readily leaks out under application of a slight pressure, whereas the liquid retained in fine pores of the inorganic powder hardly leaks out even if a pressure is applied.

The present invention will now be described in detail.

DETAILED DESCRIPTION OF THE PREFERRED EMBODIMENTS

Known organic fibers and inorganic fibers can be used as the fibrous material in the present invention without any particular limitation. As the organic fibers, there can be mentioned, for example, cellulose fibers such as rayon fibers, wood pulp fibers and cotton fibers, nylon fibers, polypropylene fibers, and polyethylene fibers. As the inorganic fibers, there can be mentioned, for example, astestos fibers, glass fibers and ceramic fibers. These organic fibers and inorganic fibers may be used singly or in combination.

Among these fibers, cellulose fibers are especially preferred because when they are formed into a shaped body according to the wet forming method described hereinafter, the adhesiveness among fibers is good and the strength can be improved in the shaped body.

The size and length of the fibrous material may be determined appropriately according to the compatibility with the inorganic powder and the strength of the resulting shaped body. Ordinarily, however, it is preferred that in the fibrous material used in the present invention, the average diameter of fibers be 0.01 to 100μ and the fiber length be 0.1 to 50 mm.

In the present invention, it is important that in the inorganic powder, the volume of fine pores having a pore radius less than 0.5μ should be at least 2.5 cc/g, preferably at least 3.0 cc/g and especially preferably at least 5.0 cc/g. As the results of statistical experiments made by us on absorption of liquids by inorganic powders, it was found that among fine pores possessed by inorganic powders, pores having a radius less than 0.5μ are important and the volume of these pores has significant influences on the liquid-absorbing characteristics of inorganic powders. In short, the liquid-retaining property and the liquid-absorbing capacity are mainly determined according to the volume of fine pores having a pore radius less than 0.5μ.

When the volume of fine pores having a pore radius less than 0.5μ is smaller than 2.5 cc/g in the inorganic powder, the liquid absorbability and liquid-retaining property of the resulting liquid-absorbing shaped body are drastically reduced and a practically applicable liquid-absorbing material cannot be obtained. In the inorganic powder, it is preferred that the above-mentioned fine pore volume be as large as possible. However, at the present, because of preparation limitations, it is ordinarily difficult to obtain an inorganic powder having a fine pore volume larger than 15 cc/g. Accordingly, an inorganic powder in which the volume of fine pores having a pore radius less than 0.5μ is 3.0 to 15 cc/g is preferably used in the present invention.

As examples of the inorganic powder preferably used in the present invention, there can be mentioned structural powders such as calcium silicate having a gyrolite type crystal structure and an SiO$_2$/CaO molar ratio of 1.6 to 6.5, preferably about 1.6 to about 4.2, a calcium silicate/calcium sulfate complex containing up to 13% by weight of calcium sulfate included in the above calcium silicate, silica obtained by an acid treatment of the above calcium silicate or calcium silicate/calcium sulfate complex and a complex of the above calcium silicate or calcium silicate/calcium sulfate complex with aluminum oxide, and mixtures of two or more of these structural powders.

The process for preparing the above-mentioned structural powders is not particularly critical, but the structural powders may be prepared according to various methods. Typical methods will now be described. For example, the above-mentioned calcium silicate is prepared according to a method in which ordinarily, a water-soluble silicate such as sodium silicate or potassium silicate is mixed with an aqueous medium of calcium chloride, calcium nitrate, unslaked lime, slaked lime or calcium sulfate and the mixture is subjected to a hydrothermal treatment at a temperature of 150° to 250° C. or a method in which insoluble silicon dioxide, for example, hydrous silica called "white carbon", or diatomaceous earth is mixed with an aqueous medium of unslaked lime or slaked lime and the mixture is subjected to a hydrothermal treatment at a temperature of 150° to 250° C. In these methods, the method using water-soluble silicate as the starting material is advantageous because calcium silicate in which the volume of fine pores having a pore radius less than 0.5μ is at least 3 cc/g, ordinarily 4.0 to 10.0 cc/g, is obtained. Accordingly, calcium silicate prepared by this method using the water-soluble silicate as the starting material is used most preferably as the inorganic powder in the present invention.

In the above-mentioned preparation method, when a water-soluble silicate is used as the starting material, the obtained calcium silicate is present in the form where amorphous silicon dioxide is complexed in the gyrolite type crystal of calcium silicate. The grain boundary face between the amorphous silicon dioxide and the calcium silicate crystal cannnot be discriminated by an electron microscope even at about 100,000 magnifications. Furthermore, the silicon dioxide cannot be separated from the crystalline calcium silicate even under dispersion by ultrasonic vibrations of 50 W. When the insoluble silicate is used as the starting material, in each of the above-mentioned methods, the silicon dioxide incorporated in the crystalline calcium silicate can be discriminated. In view of the foregoing, the calcium silicate obtained by using a water-soluble silicate as the starting material can be represented by the following general formula:

$$2CaO.3SiO_2.nSiO_2.mH_2O$$

wherein n is a number of from 0.2 to 10 and m is a positive number.

When the calcium silicate obtained by using a water-soluble silicate as the starting material is observed by an electron microscope photograph (3000 to 10000 magnifications), the form in which slices resembling petals of rose flowers are aggregated. The size and shape of such slices vary depending on the kinds of the starting materials, the ratio of the starting materials and the manufacturing conditions, but in many cases, the slices have a circular or oval shape in which the average diameter in the lengthwise direction is 0.1 to 30μ and the thickness is about 0.005 to about 0.1μ. In the instant specification, the above-mentioned calcium silicate is often referred to as "petal-like calcium silicate".

When the above-mentioned water-soluble silicate and calcium sulfate, that is, gypsum (not only gypsum dihydrate but also gypsum hemihydrate and anhydrous gypsum are included in gypsum in the instant specification), are used as the starting materials, the water-soluble silicate is gradually added to an aqueous suspension of gypsum to effect reaction and the resulting reaction mixture or a slurry formed by recovering the precipitate from the reaction mixture by filtration, washing the recovered precipitate and adding it to water is subjected to a hydrothermal treatment, whereby petal-like calcium silicate is obtained. When the molar ratio of CaSO$_4$/Na$_2$O or K$_2$O in the starting materials exceeds 1.1, a complex of the petal-like calcium silicate and gypsum is obtained. This gypsum is present in the state included in the petal-like calcium silicate as in case of the above-mentioned amorphous silicon dioxide. When the gypsum content is up to about 13% by weight, the grain boundary or structural bonding state cannot be confirmed by an electrom microscope even at 100,000 magnifications. However, if the gypsum content exceeds 13% by weight, there is ordinarily obtained a blend of the above-mentioned petal-like calcium silicate/gypsum complex and gypsum. In this blend, if the amount of gypsum blended in the calcium silicate/gypsum complex is increased, the volume of fine pores having a pore radius less than 0.5μ tends to decrease. Accordingly, it is preferred that the content of gypsum in the petal-like calcium silicate/gypsum complex be up to 13% by weight.

The petal-like calcium silicate/gypsum complex is represented by the following general formula:

$$2CaO \cdot 3SiO_2 \cdot nSiO_2 \cdot lCaSO_4 \cdot mH_2O$$

wherein n is a number of from 0.2 to 10, and m and l are positive numbers.

When the above-mentioned petal-like calcium silicate or petal-like calcium silicate/gypsum complex is reacted with aluminum sulfate $[Al_2(SO_4)_3 \cdot 18H_2O]$, a calcium silicate/aluminum oxide complex is obtained. This complex is represented by the following general formula:

$$aAl_2O_3 \cdot \frac{2-3a}{2} \cdot CaO \cdot bSiO_2 \cdot mH_2O$$

wherein a is a number of from 0.06 to 0.2, b is a number of from 1.6 to 6.5 and m is a positive number. Also this complex is preferably used as the inorganic powder in the present invention.

When the petal-like calcium silicate or petal-like calcium silicate/gypsum complex obtained according to the above-mentioned method is heated together with a mineral acid such as hydrochloric acid to forcibly extract calcium, there can be obtained silicon dioxide retaining the original petal-like shape. Also this silicon dioxide (hereinafter referred to as "petal-like silica") obtained from the petal-like calcium silicate or petal-like calcium silicate/gypsum complex is preferably used as the inorganic powder in the present invention. When this petal-like silica is observed by an electron microscope photograph (3000 to 10000 magnifications), it is confirmed that this petal-like silica is an aggregate of slices in which the average diameter in the lengthwise direction is 0.1 to $30\mu$ and the thickness is about 0.005 to about $0.1\mu$. These slices have a circular or oval shape, and in many cases, this silica is an aggregate of slices having a shape resembling a petal of a rose flower. From the results of the X-ray diffractiometry, it is confirmed that this silica is amorphous or semi-crystalline silicon dioxide.

In the manufacture of the above-mentioned petal-like calcium silicate or its complex with other compound, if the $SiO_2/CaO$ molar ratio in the starting materials is too high, as described hereinbefore with respect to the petal-like calcium silicate/gypsum complex, amorphous silicon dioxide is contained in the state blended in the petal-like calcium silicate or its complex. The presence of amorphous silicon dioxide in the blended state, that is, silicon dioxide present outside the crystal structure of the petal-like calcium silicate, tends to reduce the volume of fine pores having a pore radius less than $0.5\mu$ in the resulting petal-like calcium silicate or its complex with other compound. Therefore, it is preferred that incorporation of such blended amorphous silicon dioxide be avoided as much as possible.

In order to improve the degree of entanglement of the inorganic powder with the fibrous material, when the shaped body of the present invention is made according to the wet forming method described hereinafter, it is ordinarily preferred that in the inorganic powder, the content of particles having a size of 2 to $50\mu$ be at least 90% by weight.

The above-mentioned structural inorganic powder, especially the structural inorganic powder prepared by using a water-soluble silicate as the starting material, is preferably used as the inorganic powder in the present invention because it is excellent in the shapeability and entanglement with the fibrous material.

The liquid-absorbing shaped body of the present invention comprises the above-mentioned fibrous material and inorganic powder.

From the viewpoint of the improvement of the liquid-retaining property of the liquid-absorbing shaped body, it is preferred that the ratio of the inorganic powder to the fibrous material be as high as possible. Of course, however, in the present invention, the mixing ratio of the inorganic powder may be decided according to the intended object and use. For example, when the shaped body is used mainly for absorption of liquids, it is ordinarily preferred that the mixing ratio of the inorganic powder be increased, and when absorption of a large quantity of a liquid is not required, the mixing ratio of the inorganic powder may be reduced. Ordinarily, when absorption of a large quantity of a liquid is desired, it is preferred that in the liquid-absorbing shaped body of the present invention, the inorganic powder be contained in an amount of at least 26 parts by weight, especially at least 50 parts by weight, per 100 parts by weight of the fibrous material. Generally, when the mixing ratio of the inorganic powder is too high, liquid flow passages formed by the fibrous material are decreased and uniform absorption of the liquid becomes difficult in the resulting shaped body. Accordingly, it is ordinarily preferred that the amount of the inorganic powder present in the shaped body be smaller than 2000 parts by weight, especially smaller than 500 parts by weight, per 100 parts by weight of the fibrous material.

When absorption of a large quantity of a liquid is not required, for example, when the shaped body of the present invention is used as printing paper, it is ordinarily preferred that the inorganic powder be incorporated in an amount of 0.5 to 25 parts by weight into 100 parts by weight of pulp. In this case, a printing ink is absorbed mainly by the inorganic powder, and migration of the printing ink to the back face can effectively be prevented. Furthermore, the strength of the paper can be improved.

When the shaped body of the present invention is used mainly for absorption of liquids, it is preferred that the liquid absorbability of the shaped body be at least 5.0 cc/g. The shaped body having a retained liquid amount of at least 3.0 cc/g, especially at least 4.5 cc/g, under compression of 0.8 Kg/cm².G is most preferably used as the liquid-absorbing material.

The liquid absorbability mentioned above is a maximum amount, i.e., volume, of the liquid that can be asorbed under atmospheric pressure by the shaped body per unit weight of the shaped body, and the retained liquid amount under compression of 0.8 Kg/cm².G is a maximum amount, i.e., volume, of the liquid that can be absorbed under compression of 0.8 Kg/cm².G by the shaped body per unit weight of the shaped body. The value of the compression pressure of 0.8 Kg/cm².G is an average value of the pressure applied by the finger when the shaped body is actually used. Since the retained liquid amount under the application condition is ordinarily important, this value of the retained liquid amount under compression of 0.8 Kg/cm².G is adopted as a criterion in the present invention.

The process for preparing the liquid-absorbing shaped body of the present invention is not particularly critical. For example, there are ordinarily adopted wet forming methods such as a method in which the fibrous material is mixed with the inorganic powder in water or other solvent, the resulting slurry is shaped under suction and the shaped body is dried and a method in which the above-mentioned slurry is charged in a mold of a certain shape and the shaped body is dried, and dry forming methods such as a method in which the fibrous material is dry-blended with the inorganic powder and the mixture is press-formed. In the wet forming method such as mentioned above, in order to increase the yield of the inorganic powder to the fibrous material and prevent dusting of the shaped body, it is preferred that a molding assistant such as soluble starch or glue be used so far as the liquid-absorbing characteristics of the resulting shaped body are not reduced. Also in the wet forming method, the strength can be increased by pressing the shaped body as in case of the dry forming method. However, if the passing pressure is too high, the liquid absorbability and other liquid-absorbing characteristics are apt to be reduced. Accordingly, when pressing is carried out in the forming method, in order to maintain the liquid absorbability at a level of at least 5 cc/g, it is preferred that the pressing pressure be lower than 20 Kg/cm²·G, especially lower than 10 Kg/cm²·G.

As will readily be understood from the foregoing illustration, the liquid-absorbing shaped body of the present invention is excellent in the liquid-absorbing capacity and the liquid-retaining property to not only water but also inorganic salt aqueous solutions such as aqueous solution of sodium chloride and sodium hydroxide and organic solutions such as alcohols and edible oils.

The liquid-absorbing shaped body of the present invention can appropriately be used in various fields where absorption of liquids is required. For example, a paper-like absorbent material of the shaped body of the present invention can be used for thrown-away diapers and sanitary articles and as adsorbent paper, printing paper and blood-absorbing paper for surgical operation. Furthermore, a board-like absorbent material of the shaped body of the present invention can be used in the same fields as mentioned above with respect to the paper-like absorbent material and also as a foot wiper for a bath room. Moreover, a granular absorbent material of the shaped body of the present invention is preferably used as a horticultural water-retaining agent and a filler of an oil fence.

The present invention will now be described in detail with reference to the following Examples that by no means limit the scope of the invention.

In the following Examples and Referential Examples, the liquid absorbability and retained-liquid amount of the shaped body, and the bulk specific volume, particle size distribution, fine pore radius and fine pore volume were determined according to the following methods.

(A) Liquid Absorbability:

The weight ($W_1$) of the shaped body was measured, and the shaped body was dipped in a liquid for 3 minutes and then taken out. The shaped body was placed on a metal net of 42 mesh and allowed to stand for 5 minutes. The weight ($W_2$) of the shaped body was measured. The liquid absorbability was calculated according to the following formula:

$$\text{Liquid absorbability} = \frac{W_2 - W_1}{\rho \cdot W_1} \quad (1)$$

wherein $\rho$ stands for the density (g/cc) of the liquid.

(B) Retained-Liquid Amount:

The weight ($W_1$) of the shaped body was measured, and the shaped body was dipped in the liquid for 3 minutes and taken out. The shaped body was placed on a filter paper and pressed for 5 minutes under a pressure of P Kb/cm²·G. Then, the weight ($W_3$) of the shaped body was measured. The filter paper was used in a quantity enough to absorb water absorbed in the shaped body sufficiently. The retained-liquid amount after compression was calculated according to the following formula:

$$\text{Retained-liquid amount } (P \text{ Kg/cm}^2 \cdot G) = \frac{W_3 - W_1}{\rho \cdot W_1} \quad (2)$$

wherein $\rho$ stands for the density of the liquid.

(C) Bulk Specific Volume:

The powder was pulverized in a mortar so that 80% of particles could pass through a 200-mesh sieve, and by using the pulverized powder, the bulk specific volume was determined according to the method specified in Paragraph 6.8 of JIS K-6220.

(D) Particle Size Distribution:

The particle size distribution was determined by using Coulter Counter Model TA-II manufactured by Coulter Electronics Co.

(E) Fine Pore Radius and Fine Pore Volume:

The fine pore radius and fine pore volume were determined by using a mercury porosimeter Model 1520 manufactured by Carloerba Co. [Dilatometer Type SM3, Capillary, 3 mm in diameter, 0.07065 cm²].

REFERENTIAL EXAMPLE 1

Under atmospheric pressure, 100 cc of an aqueous solution containing 0.3144 mole/l of calcium chloride was mixed with 100 cc of an aqueous solution containing 0.3144 mole/l of sodium silicate ($SiO_2/Na_2O$ molar ratio=2.6) at 25° C. (charged $SiO_2/CaO$ molar ratio=2.6). A white precipitate was formed simultaneously with mixing, but the mixture was directly charged and sealed in an autoclave. Reaction was carried out at 200° C. for 5 hours. At this reaction, the pressure was 15 Kg/cm²·G and the water ratio was 30. The reaction mixture was filtered, and the recovered product was washed with 100 cc of deionized water 2 times and dried at 100° C. for 8 hours. The yield of the dry product was 7.35 g.

The dry product was soft and it was not contracted or solidified during the drying, and it could easily be powdered. The product was characterized by a bulk specific volume of 14.2 cc/g, and the volume of pores having a pore radius less than 0.5μ was 4.32 cc/g.

From the results of the chemical analysis, it was found that the calcium silicate obtained according to the above procedures was represented by the following formula:

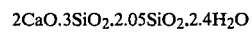

$2CaO.3SiO_2.2.05SiO_2.2.4H_2O$

When a photograph of this calcium silicate was taken by using a scanning electron microscope at 10000 magnifications and this photograph was examined, it was found that the calcium silicate was composed of an aggregate of slices having an average diameter of 2μ in the lengthwise direction and a thickness smaller than 0.1μ.

When a photograph was taken by a transmission electron microscope at 100000 magnifications and the photograph was examined, the grain boundary or bonding state could not be discriminated even though the product contained silicon dioxide.

From the results of the x-raydiffractiometry of the above calcium silicate, it was found that the calcium silicate had a gyrolite crystal structure. When 1 g of the so-obtained petal-like calcium silicate was thrown into 100 cc of water and the mixture was dispersed for 30 minutes by a desk ultrasonic washing machine (50 W), the silicon dioxide was not separated. Accordingly, it was confirmed that the silicon dioxide was not contained in the blended state but included in the crystal structure.

REFERENTIAL EXAMPLE 2

To 10 g of petal-like calcium silicate prepared in the same manner as described in Referential Example 1, 100 ml of 6 N hydrochloric acid was added, and reaction was carried out at 70° C. under atmospheric pressure. The reaction product was recovered by filtration, washed with 100 ml of deionized water 2 times and dried at 100° C. for 8 hours. The yield of the dry product was 7.75 g. The product was soft and was not contracted or solidified during the drying. The bulk specific volume of the dry product was 12.9 cc/g, and the volume of fine pores having a pore radius less than $0.5\mu$ was 3.60 cc/g.

The dry product obtained by the above procedures was silicon dioxide containing 8.5% by weight of water. When a photograph of this silicon dioxide was taken by using an electron microscope at 10000 magnifications and the photograph was examined, it was found that the product had a shape resembling that of the petal-like calcium silicate obtained in Referential Example 1.

REFERENTIAL EXAMPLE 3

In 98 cc of water, 6.5 g of gypsum dihydrate (all particles capable of passing through a 100-mesh sieve) was thrown, and the mixture was stirred for 20 minutes. Then, 100 cc of an aqueous solution containing 0.3144 mole/l of sodium silicate ($SiO_2/Na_2O$ molar ratio=2.6) was added to the slurry at a rate of 6 cc/min over a period of 16 minutes and 40 seconds under atmospheric pressure at 25° C. while the slurry was being stirred. The subsequent operations were conducted in the same manner as described in Referential Example 1 to obtain 8.2 g of a powder.

From the results of the X-ray diffractiometry, it was found that the peaks of anhydrous sypsum type II and gyrolite type calcium silicate were mingled. From the results of the chemical analysis, it was confirmed that the powder was represented by the following formula:

$$2CaO.3SiO_2.2.05SiO_2.0.20CaSO_4.2.37H_2O$$

When the powder was examined by a scanning electron microscope at 10000 magnifications, it was confirmed that the powder was composed of petals having a diameter of $2\mu$ in the lengthwise direction and a thickness smaller than $0.1\mu$. The bulk specific volume of the powder was 15.2 cc/g and the volume of fine pores having a pore radius less than $0.5\mu$ was 4.42 cc/g.

REFERENTIAL EXAMPLE 4

A 10% slurry was prepared by using 10 g of petal-like calcium silicate prepared in the same manner as described in Referential Example 1, and 40 ml of aluminum sulfate [$Al_2(SO_4)_3.18H_2O$] was gradually added and reaction was carried out for 1 hour under agitation. The reaction product was recovered by filtration, washed with 100 cc of deionized water 2 times and dried at 100° C. for 8 hours. The dry product was stable when it was dried and powdered or when it was formed into a slurry. The bulk specific volume of the dry product was 13.8 cc/g and the volume of fine pores having a pore radius less than $0.5\mu$ was 4.15 cc/g. The dry product obtained by the above procedures was a calcium silicate/aluminum oxide complex. From the results of the chemical analysis, it was confirmed that the complex was represented by the following formula:

$$0.11Al_2O_3.0.835CaO.2.52SiO_2.2.4H_2O$$

REFERENTIAL EXAMPLE 5

Calcium silicate was synthesized by using water-insoluble silicon dioxide as the starting material. Under atmospheric pressure, a 5% slurry of white carbon (4.35 g as $SiO_2$) was mixed with a 5% slurry of calcium hydroxide (2.03 g as CaO) at 25° C. for 1 hour (charged $SiO_2/CaO$ molar ratio=2.0). The mixture was charged and sealed in an autoclave and reaction was carried out at 200° C. for 15 hours. The reaction product was recovered by filtration, washed with 100 cc of deionized water 2 times and dried at 100° C. for 8 hours. The yield of the dry product was 7.91 g.

The dry product was soft and was not contracted or solidified during the drying. The bulk specific volume of the dry product was 5.8 cc/g and the volume of fine pores having a pore radius less than $0.5\mu$ was 2.6 cc/g.

It was found that the calcium silicate obtained by the above procedures was represented by the following formula:

$$CaO.1.98SiO_2.2.5H_2O$$

When a photograph of this calcium silicate was taken by using a scanning electron microscope at 5000 magnifications and the photograph was examined, it was found that the product had a shape resembling that of the petal-like calcium silicate obtained in Referential Example 1. When this calcium silicate was examined by a transmission electron microscope at 50000 magnifications, it was clearly confirmed that unreacted silicon dioxide particles were blended in the product. The unreacted silicon dioxide particles were separated according to the following procedures. More specifically, 100 cc of distilled water was added to 1 g of this calcium silicate, and the mixture was dispersed by ultrasonic vibrations in the same manner as described in Referential Example 1. The mixture was separated into a phase of unreacted silicon dioxide and a phase of calcium silicate. The unreacted silicon dioxide phase (the upper phase in this case) was removed, and when the $SiO_2/CaO$ molar ratio in the calcium silicate was determined according to the chemical analysis, it was found that this molar ratio was 1.8. Accordingly, it was confirmed that the amount of silicon dioxide blended in the calcium silicate was 4.84% by weight.

EXAMPLE 1

Inorganic powders obtained in the same manner as described in Referential Examples 1, 2, 3 and 4 were used after pulverization by Micron Mill manufactured by Hosokawa Tekkosho. The particle size distributions of the inorganic powders after pulverization are shown in Table 1.

Liquid-absorbing shaped bodies were prepared by using these inorganic powders together with a beated pulp (sulfite pulp of conifer). More specifically, a predetermined amount of the inorganic powder was incorporated and dispersed in water and the pulp was then incorporated and dispersed to obtain a slurry. A wet shaped body was prepared from this slurry by wet-forming the slurry according to the hand-made paper forming method specified in JIS P-8209. Then, a liquid-absorbing shaped body was prepared from this wet shaped body according to (A) a method in which the wet shaped body was directly dried, (B) a method in which the wet shaped body was pressed under 2.0 Kg/cm$^2$·G and was then dried or (C) a method in which are wet shaped body was dried and then pressed under 2.0 Kg/cm$^2$·G.

The amount of the inorganic powder per 100 parts by weight of the pump (absolutely dry) in the obtained liquid-absorbing shaped body and the thickness and basis weight of the liquid-absorbing shaped body are shown in Table 2. The liquid absorbability and retained-liquid amount (under atmospheric pressure and 0.8 Kg/cm$^2$·G) of the liquid-absorbing shaped body were determined to obtain results shown in Table 2. In determination of the liquid absorbability and retained liquid amount, water was used as the liquid.

It was found that the liquid-absorbing shaped bodies according to the present invention were not swollen or contracted after absorption of water and they were especially excellent in the water-retaining property under compression. Furthermore, at the time of wet forming, the retention degree of the inorganic powder was 50 to 70% based on the amounts used and the state of entanglement of the inorganic powders with the fibrous material was very good. Furthermore, dusting was substantially inhibited after shaping.

TABLE 1

| Inorganic Powder | Referential Example No. | Particles Size Distribution |
|---|---|---|
| A | 1 | content of particles of 3–40 μ = 96% by weight, average particle size = 20.2 μ |
| B | 2 | content of particles of 3–40 μ = 96% by weight, average particle size = 16.0 μ |
| C | 3 | content of particles of 3–40 μ = 97% by weight, average particle size = 20.2 μ |
| D | 4 | content of particles of 3–40 μ = 97% by weight, average particle size = 20.2 μ |

TABLE 2

| Run No. | Kind of Inorganic Powder | Forming Method | Amount (parts by weight) of Inorganic Powder | Liquid Absorbing Shaped Body Thickness (mm) | Basis Weight (g/m$^2$) | Liquid Absorbability (cc/g) | Retained Liquid Amount (cc/g) Atmospheric Pressure | 0.8 Kg/cm$^2$·G |
|---|---|---|---|---|---|---|---|---|
| 1 | — | (A) | 0 | 0.472 | 90.3 | 12.9 | 0.85 | 0.54 |
| 2 | A | (A) | 51.3 | 0.656 | 101.3 | 10.2 | 4.82 | 4.20 |
| 3 | A | (A) | 130.6 | 0.805 | 98.6 | 10.9 | 6.01 | 5.50 |
| 4 | A | (A) | 253.2 | 0.902 | 97.3 | 13.4 | 6.30 | 5.81 |
| 5 | A | (A) | 538.2 | 0.983 | 102.5 | 16.2 | 8.20 | 7.42 |
| 6 | A | (B) | 230.2 | 0.526 | 98.1 | 12.1 | 4.26 | 3.45 |
| 7 | A | (C) | 242.5 | 0.513 | 99.9 | 12.6 | 4.32 | 3.72 |
| 8 | B | (A) | 103.2 | 0.784 | 98.4 | 11.5 | 6.05 | 5.41 |
| 9 | B | (A) | 250.5 | 0.912 | 99.6 | 14.2 | 6.50 | 5.98 |
| 10 | B | (A) | 350.3 | 0.952 | 97.9 | 15.8 | 7.67 | 6.45 |
| 11 | B | (B) | 230.3 | 0.512 | 99.8 | 12.0 | 4.59 | 3.99 |
| 12 | B | (C) | 233.1 | 0.502 | 97.9 | 13.1 | 5.05 | 4.02 |
| 13 | C | (A) | 109.3 | 0.769 | 102.3 | 12.1 | 6.01 | 5.42 |
| 14 | C | (A) | 245.2 | 0.900 | 99.8 | 14.3 | 6.64 | 6.02 |
| 15 | C | (A) | 420.9 | 0.983 | 97.8 | 16.2 | 7.98 | 7.06 |
| 16 | C | (B) | 250.3 | 0.522 | 98.5 | 11.9 | 5.02 | 4.52 |
| 17 | C | (C) | 252.2 | 0.531 | 99.2 | 12.2 | 5.62 | 4.38 |
| 18 | D | (A) | 103.7 | 0.752 | 95.9 | 12.2 | 6.20 | 5.42 |
| 19 | D | (A) | 246.5 | 0.912 | 96.3 | 14.5 | 6.76 | 5.89 |
| 20 | D | (A) | 390.8 | 0.973 | 98.2 | 17.2 | 7.87 | 6.72 |

Note
Run No. 1 in Table 2 was a comparative run

EXAMPLE 2

The liquid absorbability and retained liquid amount of the liquid-absorbing shaped body obtained in Example 1 (run No. 4 of Table 2) to a 5% by weight aqueous solution of sodium chloride, a 5% by weight aqueous solution of sodium hydroxide, an edible oil and ethanol were determined to obtain results shown in Table 3. As is apparent from Table 3, good results were obtained irrespectively of the kind of the liquid, similarly as in the case of water. The liquid-absorbing rate at this test was such that when 10 cc of the liquid per g of the liquid-absorbing shaped body was dropped in a moment, the liquid was homogeneously absorbed within 10 seconds.

TABLE 3

| Run No. | Liquid | Liquid Absorbability (cc/g) | Retained Liquid Amount (cc/g) Atmospheric Pressure | 0.8 Kg/cm$^2$·G |
|---|---|---|---|---|
| 1 | 5% NaCl | 13.2 | 6.20 | 5.81 |
| 2 | 5% NaOH | 14.0 | 6.30 | 5.82 |
| 3 | edible oil | 11.2 | 6.10 | 5.79 |
| 4 | ethanol | 13.1 | 6.32 | 5.83 |

EXAMPLE 3

Liquid-absorbing shaped bodies were prepared by using the inorganic powder A of Example 1 shown in Table 1 and cotton or glass fibers as the fibrous material according to the forming method (B) or (C) described in Example 1. The amount of the inorganic powder per 100 parts by weight of the fibrous material (absolutely dry) in the liquid-absorbing shaped body and the thickness and basis weight of the shaped body are shown in Table 4. The liquid absorbability and retained liquid amount (under atmospheric pressure and 0.8 Kg/cm²·G) were determined to obtain results shown in Table 4. Water was used as the liquid.

TABLE 4

| Run No. | Fibrous Material | Forming Method | Amount (parts by weight) of Inorganic Powder | Liquid-Absorbing Shaped Body Thickness (mm) | Basis Weight (g/m²) | Liquid Absorbability (cc/g) | Retained Liquid Amount (cc/g) Atmospheric Pressure | 0.8 Kg/cm²·G |
|---|---|---|---|---|---|---|---|---|
| 1 | cotton fibers | (B) | 129.2 | 0.432 | 98.2 | 10.2 | 5.80 | 5.21 |
| 2 | cotton fibers | (B) | 252.2 | 0.501 | 101.3 | 12.2 | 6.25 | 5.62 |
| 3 | cotton fibers | (B) | 401.3 | 0.600 | 102.2 | 14.3 | 6.91 | 6.42 |
| 4 | cotton fibers | (C) | 253.9 | 0.482 | 98.8 | 12.3 | 5.92 | 5.57 |
| 5 | glass fibers | (B) | 135.3 | 0.401 | 100.2 | 11.5 | 5.32 | 4.91 |
| 6 | glass fibers | (B) | 248.3 | 0.452 | 98.5 | 12.8 | 6.12 | 5.62 |
| 7 | glass fibers | (C) | 128.5 | 0.388 | 97.3 | 12.1 | 5.45 | 4.84 |
| 8 | glass fibers | (C) | 254.2 | 0.442 | 105.2 | 12.5 | 6.21 | 5.43 |

EXAMPLE 4

Board-like liquid-absorbing shaped bodies were prepared from the inorganic powder A of Example 1 shown in Table 1 and a pulp (sulfite pulp of conifer) or glass fibers as the fibrous material according to (D) a method in which a wet shaped body was formed from the inorganic powder and fibrous material by wet forming in the same manner as described in Example 1, the wet shaped body was pressed under 4.5 Kg/cm²·G and the pressed wet shaped body was dried at 100° C. for 4 hours, or (E) a method in which the inorganic powder was dry-blended with the fibrous material and the mixture was pressed under 4.5 Kg/cm²·G. The amount of the inorganic powder per 100 parts by weight of the fibrous material (absolutely dry) in the liquid-absorbing shaped body and the thickness and basis weight of the shaped body are shown in Table 5. The liquid absorbability and retained liquid amount (under atmospheric pressure and 0.8 Kg/cm²·G) were determined to obtain results shown in Table 5. Water was used as the liquid. As is apparent from the results shown in Table 5, also the liquid-absorbing shaped bodies prepared by pressing under 4.5 Kg/cm²·G had excellent liquid-absorbing characteristics. When the absorbing characteristics of these shaped bodies to a 5% aqueous solution of sodium chloride and edible oil were tested in the same manner as in Example 2, results quite similar to those obtained in Example 2 were obtained.

TABLE 5

| Run No. | Fibrous Material | Forming Method | Amount (parts by weight) of Inorganic Powder | Liquid-Absorbing Shaped Body Thickness (mm) | Basis Weight (g/m²) | Liquid Absorbability (cc/g) | Retained Liquid Amount (cc/g) Atmospheric Pressure | 0.8 Kg/cm²·G |
|---|---|---|---|---|---|---|---|---|
| 1 | pulp | (D) | 150.2 | 1.52 | 420.5 | 6.71 | 5.00 | 4.20 |
| 2 | pulp | (E) | 149.3 | 1.50 | 420.3 | 6.50 | 4.82 | 4.21 |
| 3 | glass fibers | (D) | 148.2 | 1.49 | 432.5 | 5.91 | 4.52 | 4.02 |
| 4 | glass fibers | (E) | 153.3 | 1.45 | 431.0 | 5.62 | 4.42 | 4.00 |

EXAMPLE 5

The petal-like calcium silicate prepared in Referential Example 1, which was used in Example 1, was used as the inorganic powder, and a pulp (sulfite pulp of conifer) or glass fibers were used as the fibrous material. A shaped body of a columnar form was prepared by dry-blending 100 parts of the fibrous material with 200 parts of the petal-like calcium silicate to form a homogeneous dispersion, charging the dispersion into a mold and press-molding the dispersion under 4.5 Kg/cm²·G. The height and weight of the so obtained columnar liquid-absorbing shaped body are shown in Table 6. The liquid absorbability and retained liquid amount of the shaped body were determined. The obtained results are shown in Table 6.

TABLE 6

| Run No. | Fibrous Material | Shaped Body Height (mm) | Weight (g) | Liquid Absorbability (cc/g) | Retained Liquid Amount (cc/g) Atmospheric Pressure | 0.8 Kg/cm²·G |
|---|---|---|---|---|---|---|
| 1 | pulp | 3.01 | 0.007 | 6.03 | 5.03 | 4.35 |
| 2 | glass fibers | 3.00 | 0.007 | 5.95 | 5.00 | 4.22 |

EXAMPLE 6

Calcium silicate prepared in the same manner as described in Referential Example 5 was pulverized by Micron Mill to form an inorganic powder having an average particle size of 20.2μ. A paper-like shaped body was prepared in the same manner as in Example 1 according to the forming method (A) except that the above-mentioned pulverized calcium silicate was used as the inorganic powder.

The amount of the inorganic powder per 100 parts by weight of the fibrous material (absolutely dry) in the shaped body and the thickness and basis weight of the shaped body are shown in Table 7. The liquid absorbability and retained liquid amount of the shaped body were determined to obtain results shown in Table 7. Water was used as the liquid.

TABLE 7

| | Run No. 1 | Run No. 2 |
|---|---|---|
| Inorganic Material | calcium silicate | calcium silicate |
| Forming Method | (A) | (A) |
| Amount (parts by weight) of Inorganic Powder | 90.2 | 142.3 |
| Shaped Body | | |
| Thickness (mm) | 0.790 | 0.823 |
| Basis Weight (g/m$^2$) | 97.8 | 98.3 |
| Liquid Absorbability (cc/g) | 10.3 | 10.8 |
| Retained Liquid Amount (cc/g) | | |
| Atmospheric Pressure | 4.06 | 4.95 |
| 0.8 Kg/cm$^2$ . G | 3.81 | 4.23 |

EXAMPLE 7

The retained liquid amounts (under atmospheric pressure) of conventional absorbent materials, that is, absorbent paper and starch-acrylic acid ester copolymer, to various liquids were measured to obtain results shown in Table 8. As will readily be understood from the results shown in Table 8, an absorbent material showing high liquid-absorbing characteristics to all the liquids has not been developed. It was confirmed that the liquid-absorbing speed of the starch-acrylic acid ester copolymer was about ⅓ to about ½ of the absorbent paper.

TABLE 8

| | Retained Liquid Amount (cc/g) (under atmospheric pressure) | | | | |
|---|---|---|---|---|---|
| Run No. | Absorbent Material | 5% aqueous solution of sodium chloride | 5% aqueous solution of sodium hydroxide | edible oil | etha-nol | water |
| 1 | absorbent paper | 1.20 | 1.12 | 1.18 | 1.02 | 1.22 |
| 2 | starch-acrylic acid ester copolymer | 4.92 | 4.32 | 0.10 | 0.10 | 5.43 |

EXAMPLE 8

Paper-like shaped bodies having too small an amount of an inorganic powder were prepared by using the inorganic powder A of Example 1 shown in Table 1 according to the forming methods (A) and (B). The amount of the inorganic powder per 100 parts by weight of the fibrous material (absolutely dry) in the shaped body and the thickness and basis weight of the shaped body are shown in Table 9. The liquid absorbability and retained liquid amount (under atmospheric pressure and 0.8 Kg/cm$^2$·G) were determined to obtain results shown in Table 9.

TABLE 9

| | Run No. 1 | Run No. 2 |
|---|---|---|
| Forming Method | (A) | (B) |
| Amount (parts by weight) of Inorganic Powder | 20.5 | 20.3 |
| Shaped Body | | |
| Thickness (mm) | 0.582 | 0.172 |
| Basis Weight (g/m$^2$) | 100.5 | 99.7 |
| Liquid Absorbability (cc/g) | 13.5 | 3.6 |
| Retained Liquid Amount (cc/g) | | |
| Atmospheric Pressure | 2.56 | 2.01 |
| 0.8 Kg/cm$^2$ . G | 1.78 | 1.56 |

EXAMPLE 9

The petal-like calcium silicate having an SiO$_2$/CaO molar ratio of 2.52, which was obtained in Referential Example 1, was pulversed by Micron Mill manufactured by Hosokawa Tekkosho so that the current of particles having a size of 2 to 30μ was 97% by weight and the average particle size was 16μ, and the pulverized calcium silicate was used as a loading. Aluminum sulfate [Al$_2$(SO$_4$)$_3$.18H$_2$O] was added to an beated pulp in an amount of 2.0% by weight based on the pulp (absolutely dry). Incidentally, the amount of the pulp was fixed so that the basis weight of the loading-free paper was 48 g/m$^2$. Then, the loading in the form of a slurry was added to the pulp, and a paper was made according to the method for preparing a hand-made paper, specified by JIS P-8209. The amount [% by weight based on the pulp (absolutely dry)] of the loading is shown in Table 10.

Papers were prepared in the same manner as described above by using the petal-like silica obtained in Referential Example 2, the petal-like calcium silicate-gypsum complex obtained in Referential Example 3 and the petal-like calcium silicate/aluminum oxide complex obtained in Referential Example 4 as loadings.

For comparison, a paper was similarly prepared without addition of any loading.

These papers were tested to obtain results shown in Table 10.

From the results shown in Table 10, it will readily be understood that the petal-like loadings according to the present invention are excellent in the effects of moderating reduction of the breaking strength and preventing migration of an ink to the back face and furthermore, they exert a function of improving the whiteness and opacity. Moreover, it was found that since the petal-like loadings according to the present invention are composed of relatively loosely aggregated particles where impurities are not substantially incorporated, wires are not substantially worn during the paper-making operation.

Incidentally, run No. 1 in Table 10 was a comparative run where no loading was used.

TABLE 10

| Run No. | Loading (Referential Example No.) | Amount Added (%) | Basis Weight (g/m²) | Thickness (mm) (average value) | Whiteness (%) | Opacity (%) | Breaking Length* | Pore Volume (cc/g) below 0.75μ | Pore Volume (cc/g) above 7.5μ | Whiteness after Printing*** (%) 8.5 g/m²** | Whiteness after Printing*** (%) 4.0 g/m²** |
|---|---|---|---|---|---|---|---|---|---|---|---|
| 1 | — | 0 | 48.0 | 0.079 | 68 | 64.5 | 1.0 | 0.05 | 0.110 | 16.2 | 32.0 |
| 2 | 1 | 4.0 | 49.8 | 0.080 | 71.2 | 71.4 | 0.9 | 0.191 | 0.112 | 42.1 | 53.5 |
| 3 | 1 | 7.8 | 51.5 | 0.083 | 74.1 | 75.2 | 0.8 | 0.324 | 0.120 | 58.2 | 61.8 |
| 4 | 1 | 10.0 | 52.5 | 0.086 | 75.7 | 77.5 | 0.77 | 0.402 | 0.131 | 65.2 | 66.7 |
| 5 | 2 | 3.4 | 49.5 | 0.079 | 70.6 | 68.1 | 0.9 | 0.125 | 0.132 | 30.2 | 38.6 |
| 6 | 2 | 5.6 | 50.4 | 0.082 | 72.4 | 70.6 | 0.8 | 0.186 | 0.155 | 37.2 | 47.2 |
| 7 | 2 | 7.1 | 51.2 | 0.083 | 73.6 | 71.9 | 0.74 | 0.205 | 0.172 | 43.5 | 55.9 |
| 8 | 3 | 4.1 | 49.8 | 0.080 | 71.2 | 71.4 | 0.9 | 0.192 | 0.113 | 42.2 | 53.6 |
| 9 | 3 | 7.8 | 51.5 | 0.082 | 74.3 | 75.4 | 0.8 | 0.323 | 0.121 | 58.2 | 61.9 |
| 10 | 3 | 10.1 | 52.6 | 0.084 | 75.8 | 77.9 | 0.77 | 0.409 | 0.133 | 66.0 | 67.0 |
| 11 | 4 | 4.2 | 49.9 | 0.081 | 71.9 | 71.5 | 0.9 | 0.192 | 0.114 | 42.3 | 53.9 |
| 12 | 4 | 8.0 | 51.6 | 0.083 | 74.2 | 75.5 | 0.8 | 0.322 | 0.129 | 59.0 | 61.2 |
| 13 | 4 | 10.9 | 52.9 | 0.084 | 76.0 | 78.0 | 0.77 | 0.412 | 0.130 | 65.8 | 66.9 |

Note
*relative value calculated based on the supposition that the breaking length (5.93 Km) of the loading-free paper was 1
**the amount of the ink received
***the whiteness of the surface opposite to the printed surface

What we claim is:

1. A shaped body excellent in the liquid-absorbing property, which comprises a fibrous material and an inorganic powder composed of aggregated slices in which the volume of fine pores having a pore radius less than 0.5μ is at least 2.5 cc/g.

2. A shaped body as set forth in claim 1, wherein the inorganic powder is contained in an amount of 0.5 to 2000 parts by weight per 100 parts by weight of the fibrous material.

3. A shaped body as set forth in claim 1, wherein the inorganic powder is contained in an amount of 26 to 2000 parts by weight per 100 parts by weight of the fibrous material.

4. A shaped body as set forth in claim 1, wherein the inorganic powder is contained in an amount of 0.5 to 25 parts by weight per 100 parts by weight of the fibrous material.

5. A shaped body as set forth in claim 1, wherein in the inorganic powder, the volume of fine pores having a pore radius less than 0.5μ is at least 3.0 cc/g.

6. A shaped body as set forth in claim 1, wherein the inorganic powder is an aggregate of slices having an average diameter of 0.1 to 30μ in the longitudinal direction and a thickness of 0.005 to 0.1μ.

7. A shaped body as set forth in claim 1, wherein the inorganic powder is at least one member selected from the group consisting of calcium silicate having a gyrolite crystal structure in which the $SiO_2/CaO$ molar ratio is 1.6 to 6.5, a calcium silicate/calcium sulfate complex consisting of said calcium silicate and up to 13% by weight of calcium sulfate included therein, silica obtained by an acid treatment of said calcium silicate or said calcium silicate/calcium sulfate complex and a complex of said calcium silicate or said calcium silicate/calcium sulfate complex with aluminum oxide.

8. A shaped body as set forth in claim 7, wherein the calcium silicate contains amorphous silicon dioxide included in the crystal thereof.

9. A shaped body as set forth in claim 1 which is in the form of a paper.

10. A shaped body as set forth in claim 1 which is in the form of a board.

11. A shaped body as set forth in claim 1 which is in the granular form.

12. A shaped body as set forth in claim 1, wherein the fibrous material is composed of cellulose fibers.

13. A shaped body as set forth in claim 1, wherein the fibrous material and inorganic powder are uniformly dispersed.

* * * * *